(12) United States Patent
Namavari et al.

(10) Patent No.: US 9,011,817 B2
(45) Date of Patent: Apr. 21, 2015

(54) COMPOUNDS AND METHODS OF MAKING COMPOUNDS

(75) Inventors: Mohammad Namavari, South San Francisco, CA (US); Sanjiv Sam Gambhir, Portola Valley, CA (US); Beverly S. Mitchell, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 864 days.

(21) Appl. No.: 12/875,339

(22) Filed: Sep. 3, 2010

(65) Prior Publication Data

US 2011/0059014 A1    Mar. 10, 2011

Related U.S. Application Data

(60) Provisional application No. 61/239,536, filed on Sep. 3, 2009.

(51) Int. Cl.
*A61K 51/00* (2006.01)
*A61M 36/14* (2006.01)
*C07H 19/16* (2006.01)

(52) U.S. Cl.
CPC ................................. *C07H 19/16* (2013.01)

(58) Field of Classification Search
CPC ............................ A61K 51/00; A61K 36/14
USPC ........................................... 424/1.73
See application file for complete search history.

(56) References Cited

PUBLICATIONS

Jenny et al. (Tetrahedron. Lett. 1991, 32, 7029-7032).*
Kim et al. (J. Pharm. Sci. 1996, 85, 339-344).*
Crouzel et al. (J. Labelled Compd. Radiopharm. 1989, XXVII, 1007-1013).*
Bolton (J. Labelled Compd. Radiopharm. 2002, 45, 485-528).*
Wang et al. (J. Org. Chem. 2000, 65, 5969-5985).*
Pankiewicz et al. (J. Org. Chem. 1992, 57, 553-559).*
Montgomery et al. (J. Med. Chem. 1986, 29, 2389-2392).*
Wikipedia Guanosine 2014.*

* cited by examiner

*Primary Examiner* — Michael G Hartley
*Assistant Examiner* — Melissa Perreira
(74) *Attorney, Agent, or Firm* — Thomas|Horstemeyer, LLP

(57) ABSTRACT

Embodiments of the present disclosure provide for compounds and methods of making compounds such as those shown in FIGS. 1.1A and 1.1B having formula 2, 3, 4, 5, 11, and 12 and formula 2', 4', and 11', as well as uses for the compounds for imaging, and the like.

10 Claims, 13 Drawing Sheets

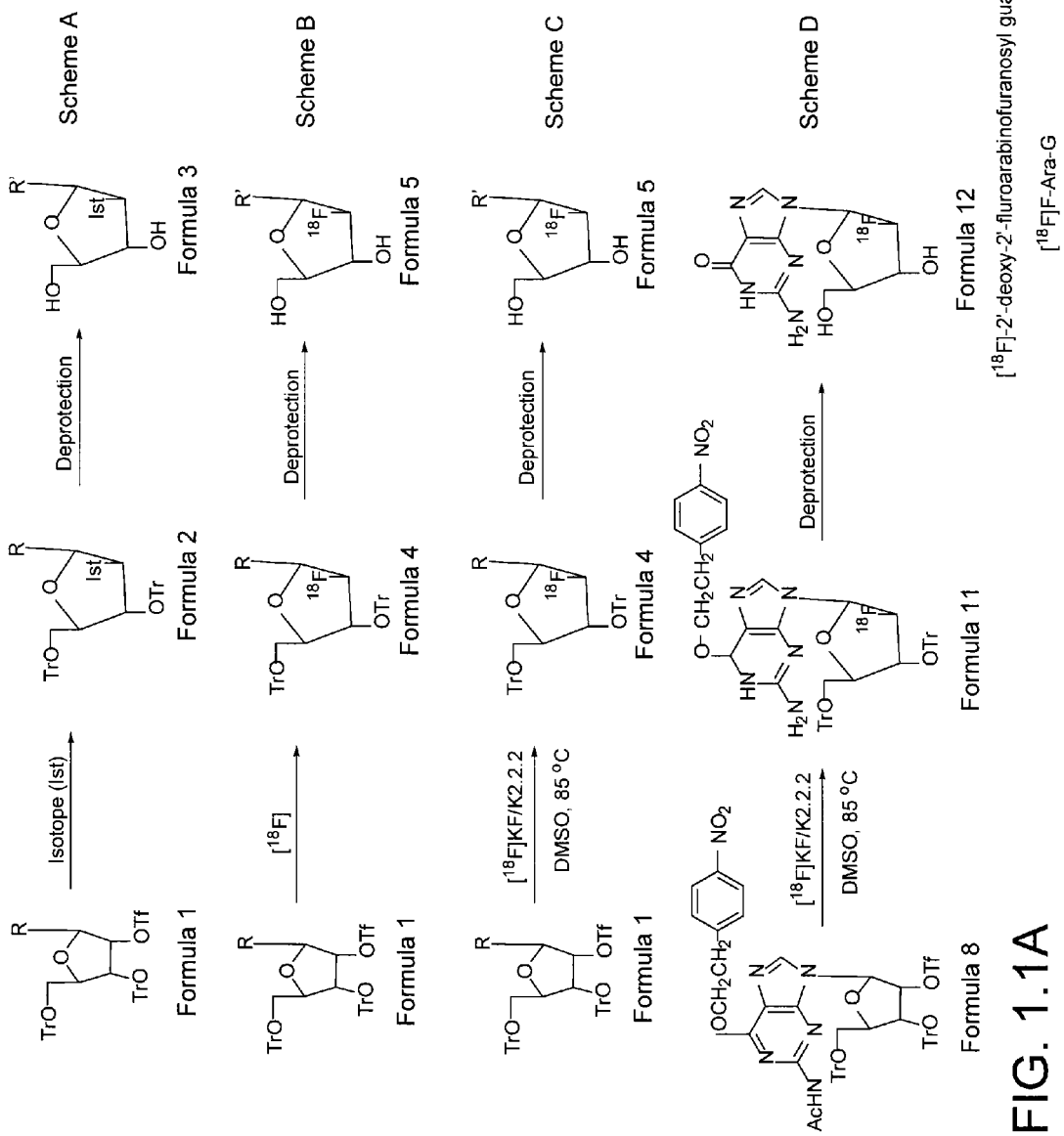
FIG. 1.1A

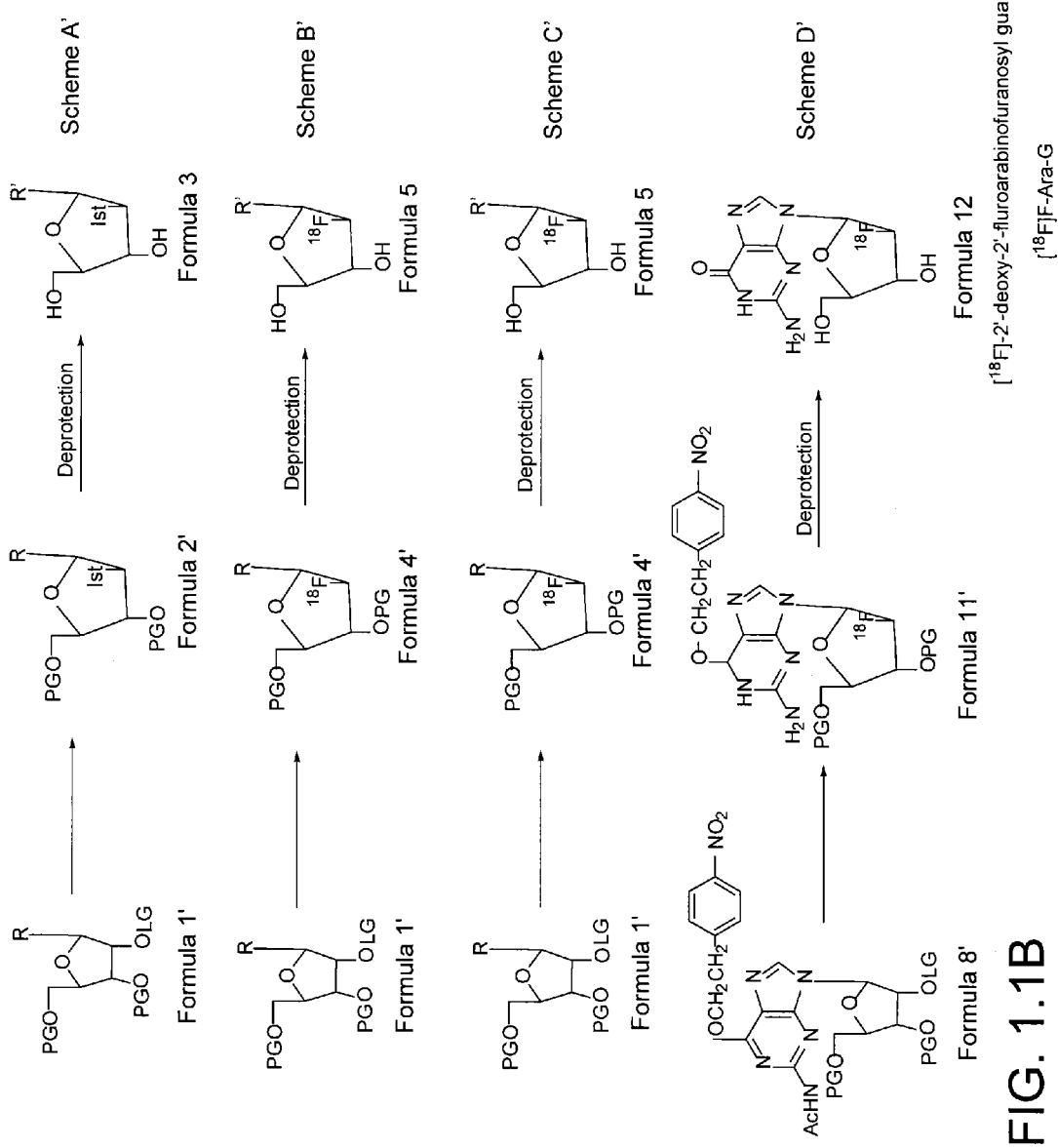
FIG. 1.1B

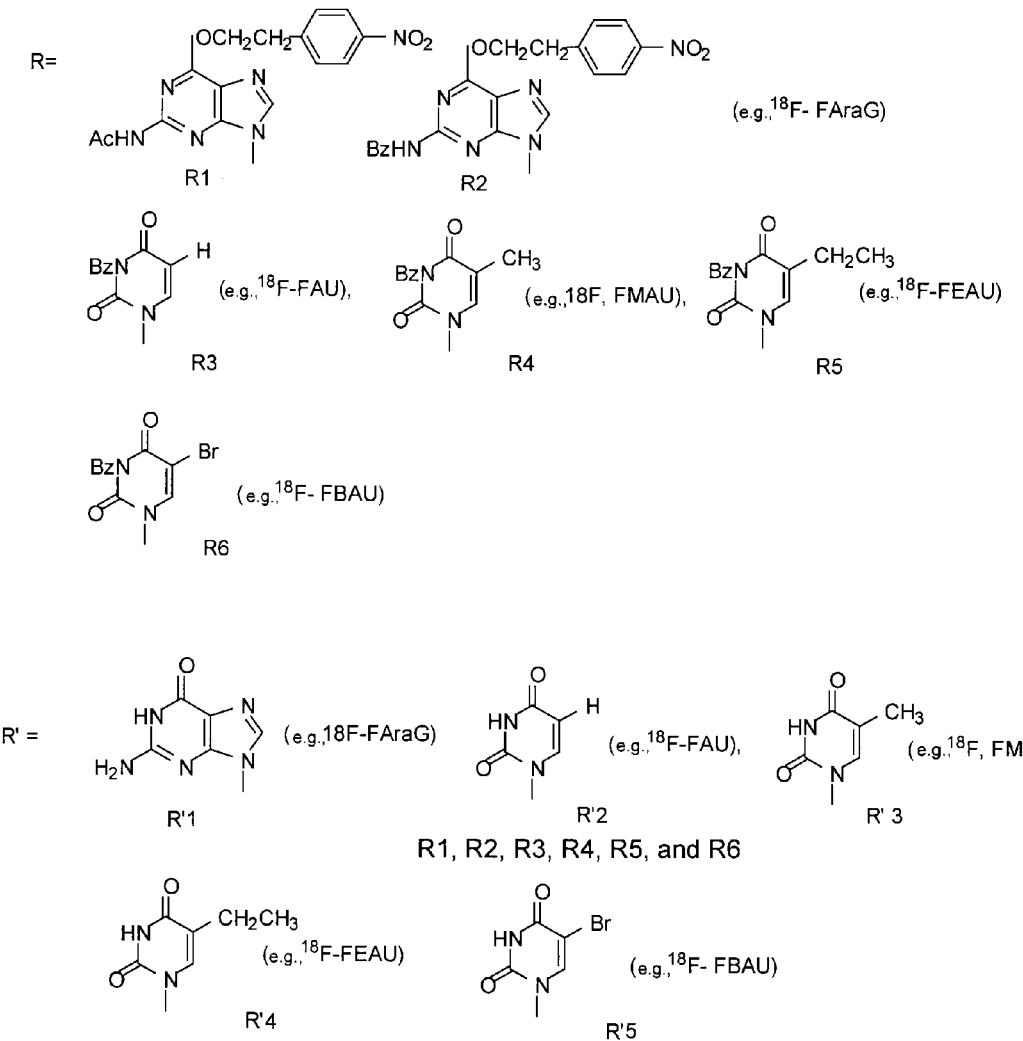
FIG. 1.2

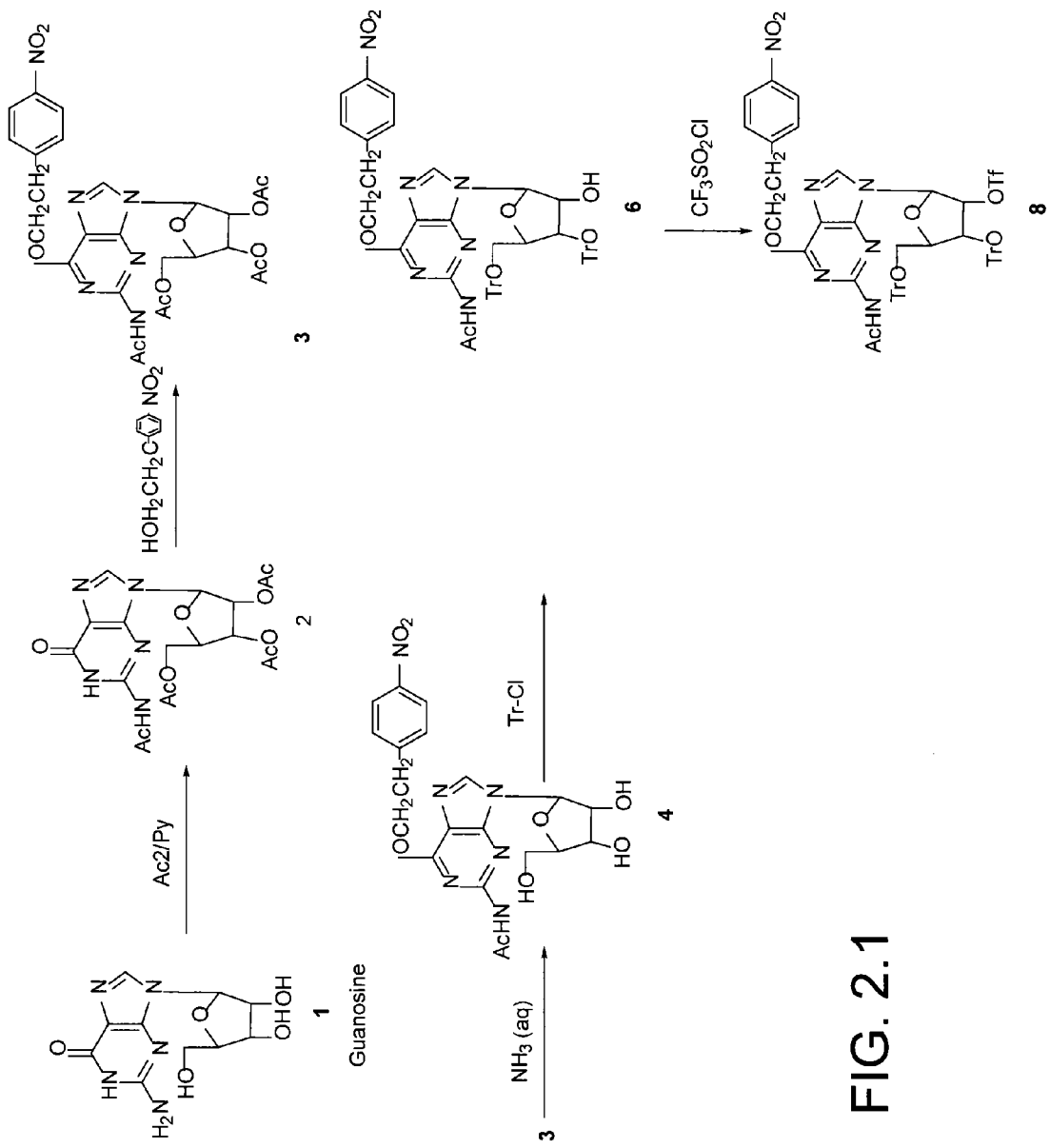
FIG. 2.1

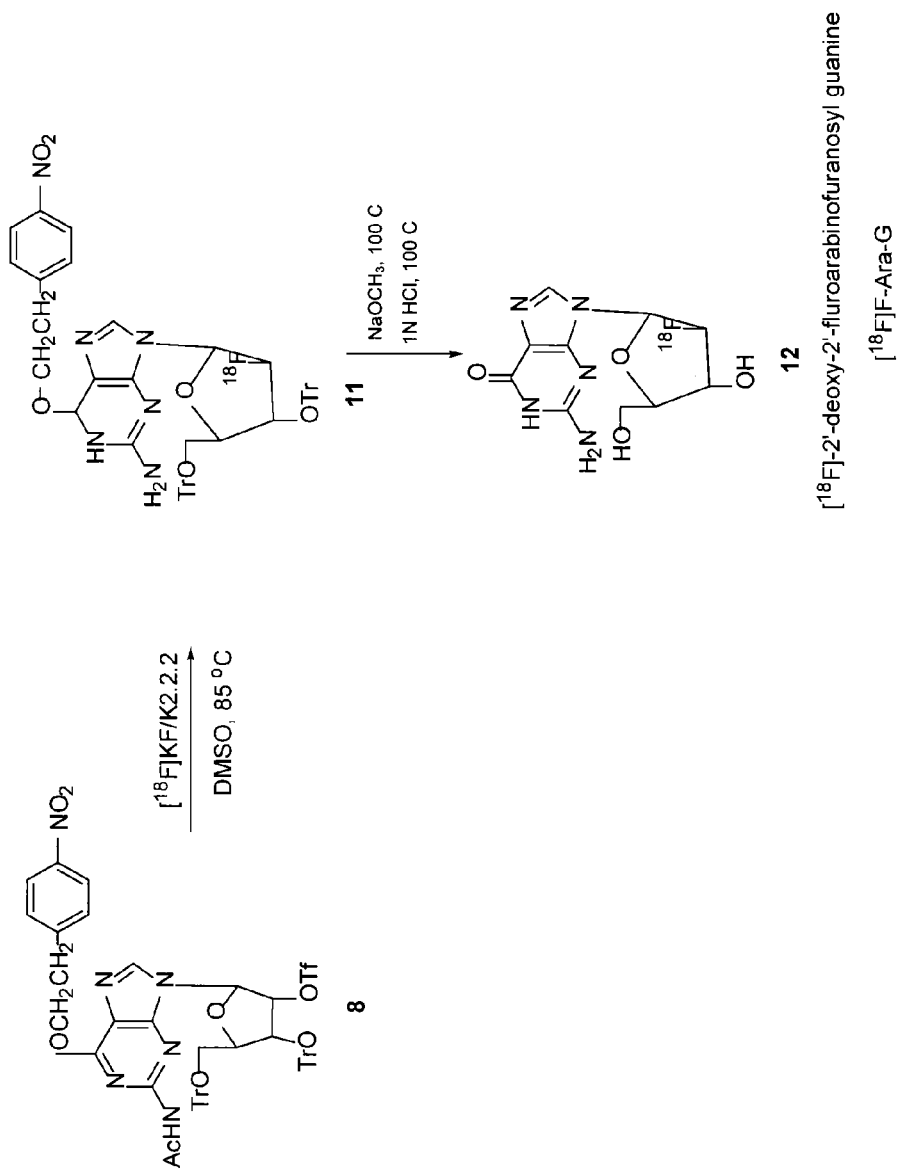
FIG. 2.1 (cont)

Figure 2.2: Uptake of $^{18}$F-AraG by CEM T lymphoblasts and primary thymocytes
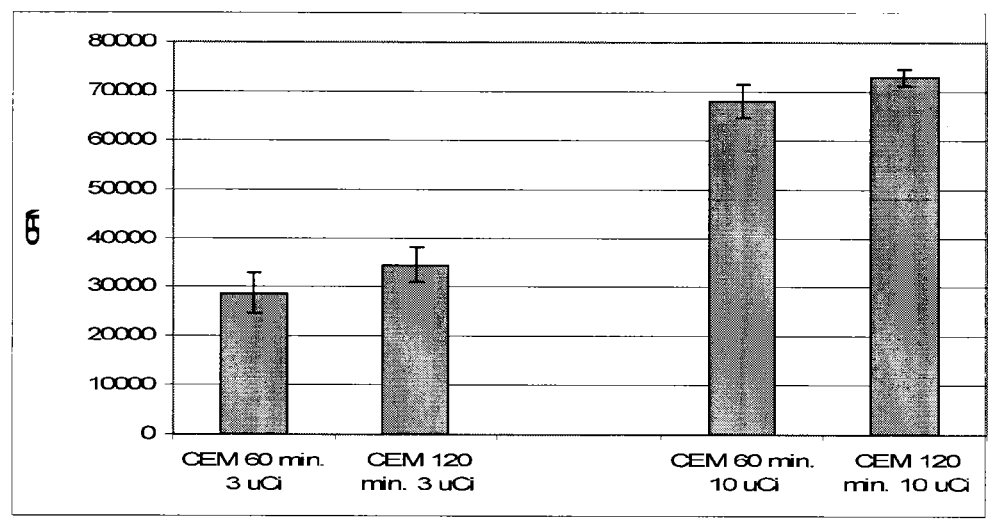
FIG. 2.2

Figure 2.3 : Competition of cold 2F AraG with 8-[$^3$H]AraG for uptake into cells
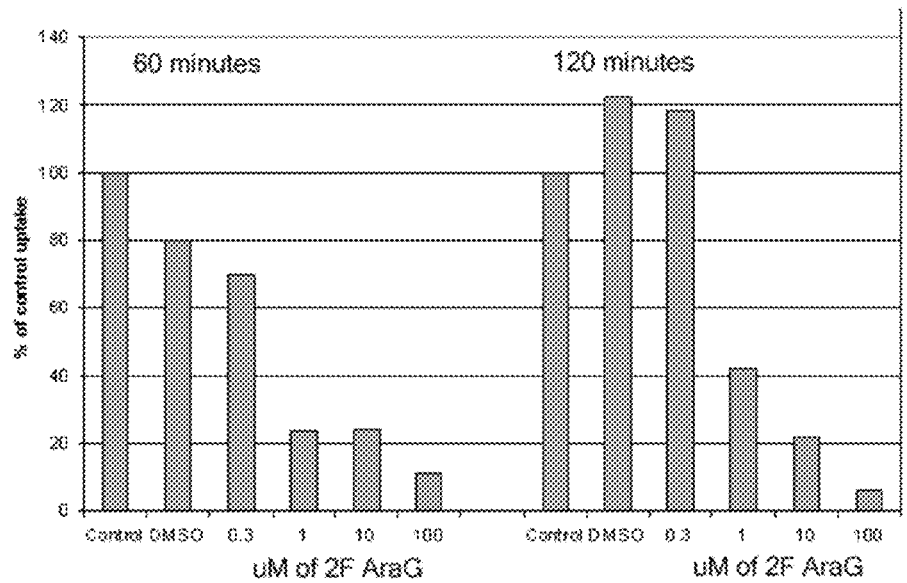
FIG. 2.3A
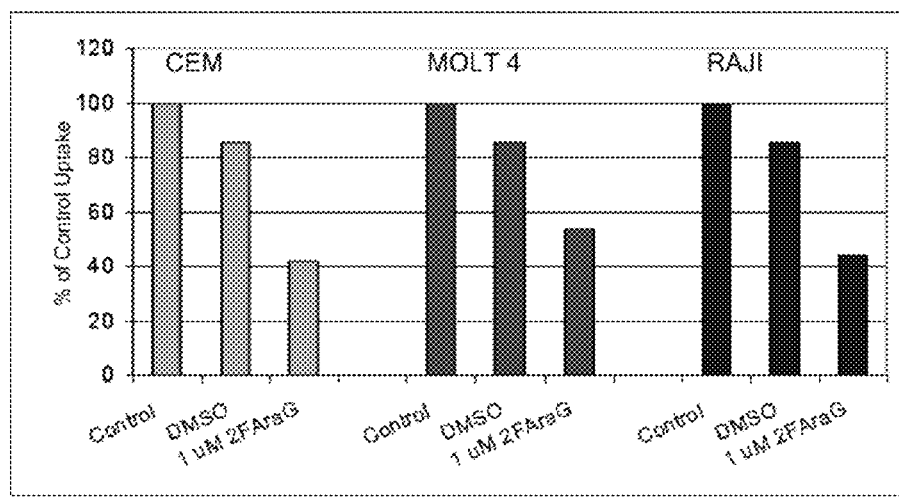
FIG. 2.3B

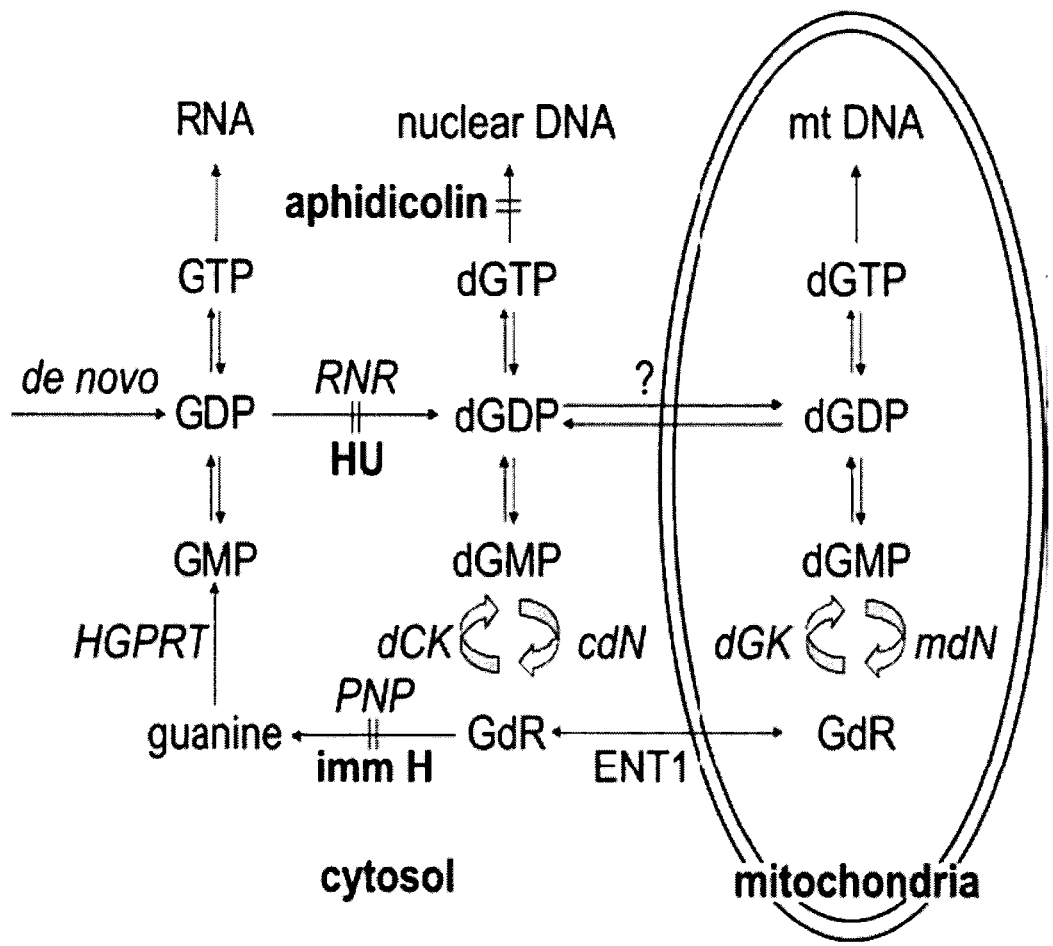
Figure 2.4: Metabolism of 2'-deoxyguanosine
FIG. 2.4

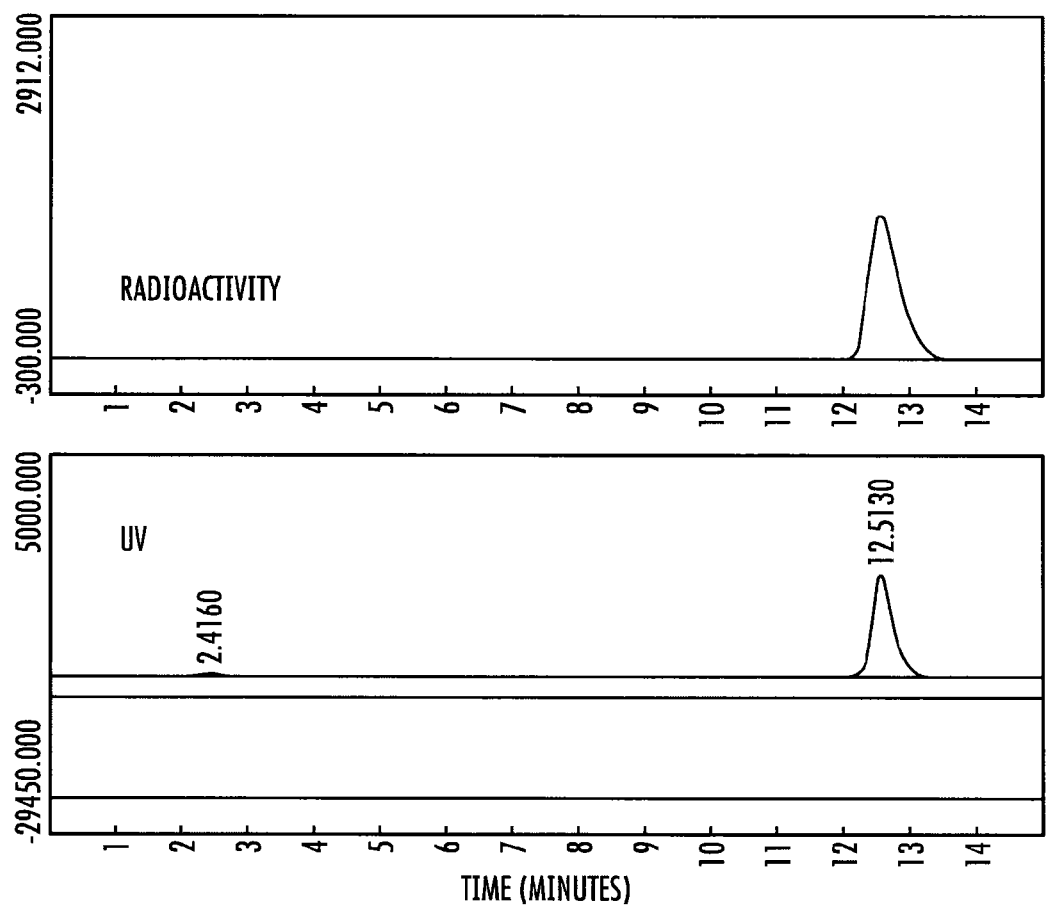
FIG. 3.1

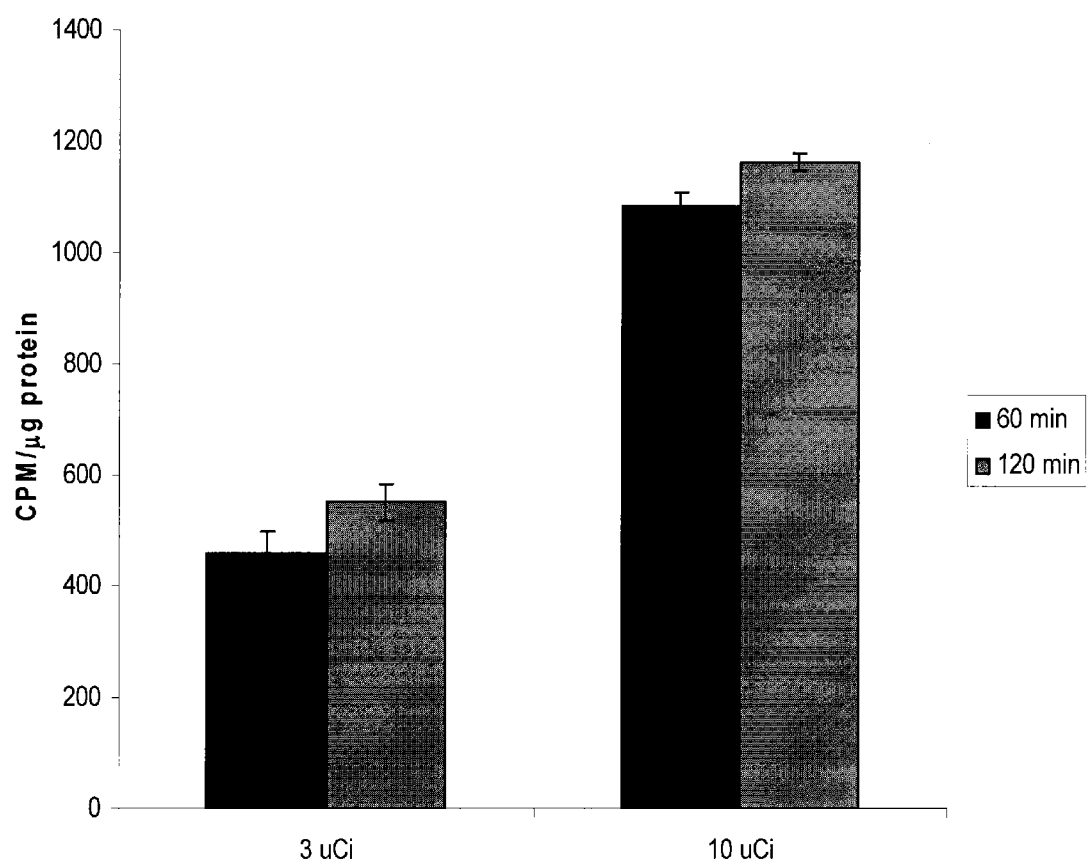
FIG. 3.2

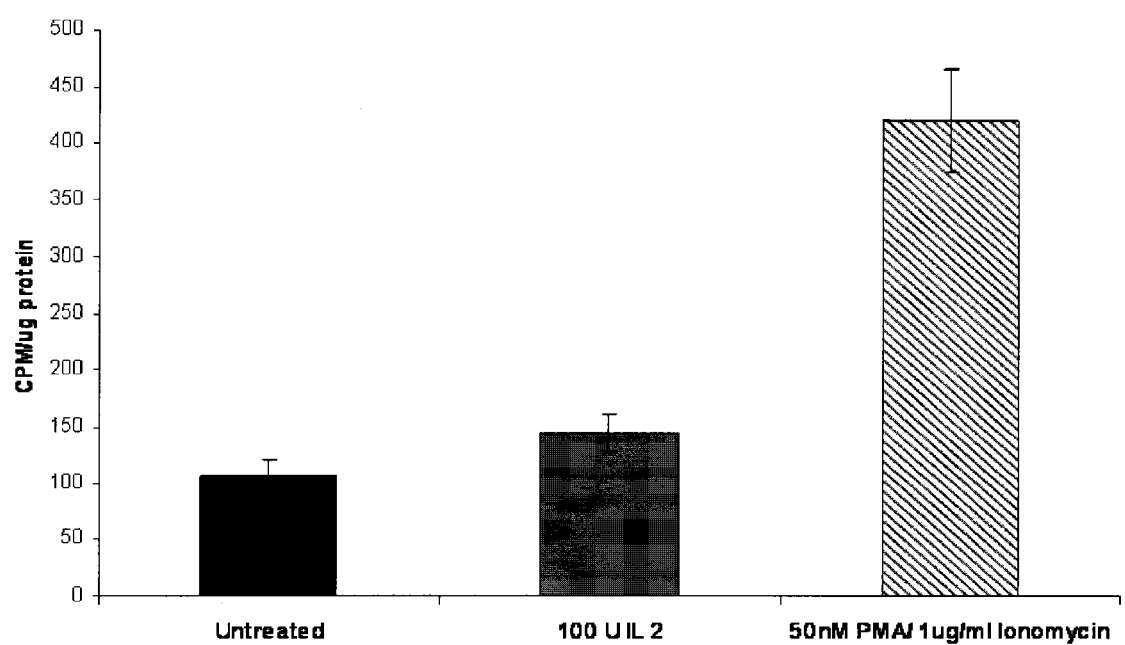
FIG. 3.3

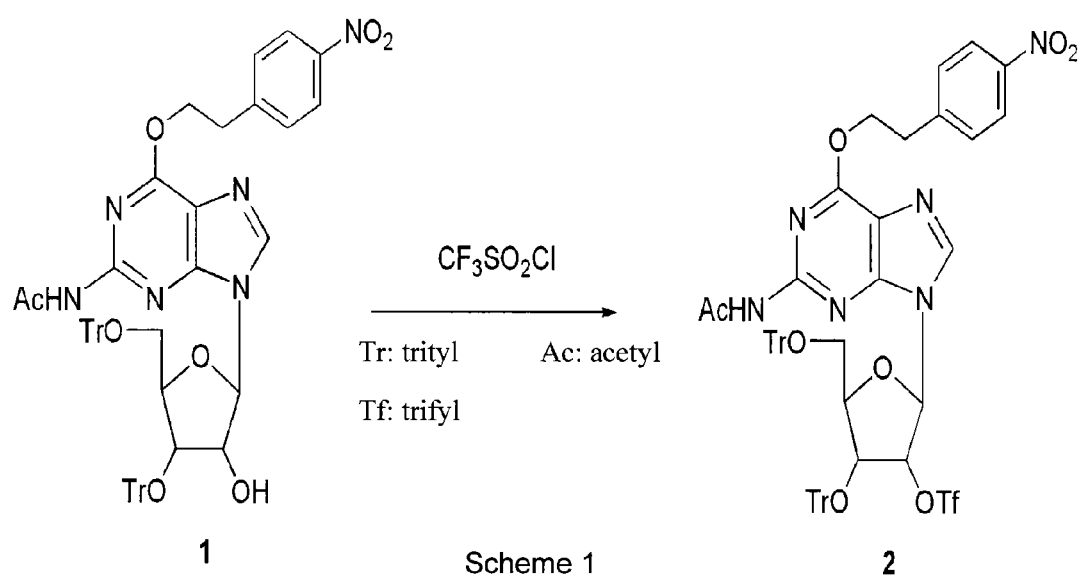
FIG. 3.4

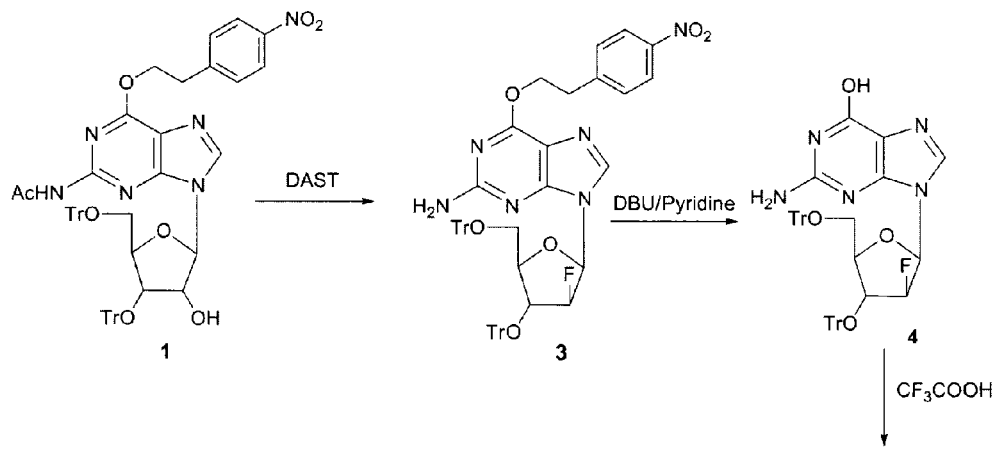
Scheme 2
FIG. 3.5
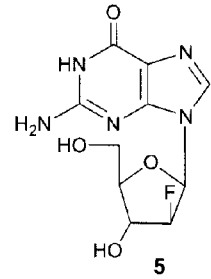
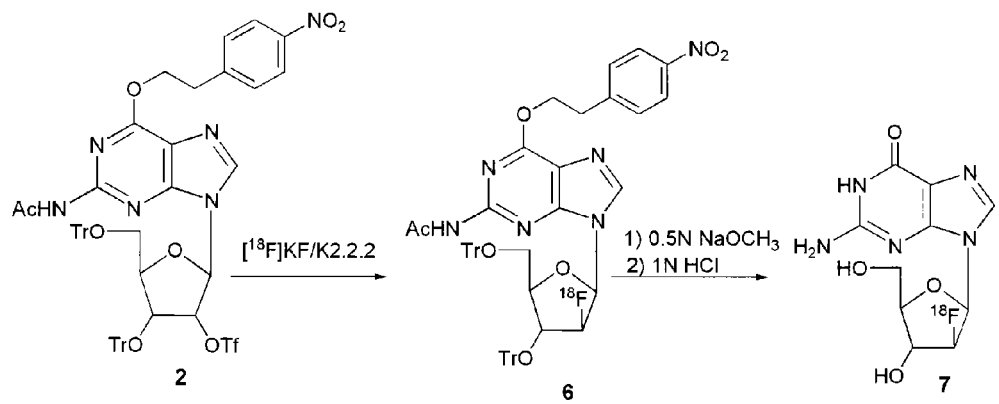
Scheme 3
FIG. 3.6

COMPOUNDS AND METHODS OF MAKING COMPOUNDS

CROSS-REFERENCE TO RELATED APPLICATIONS

This application claims priority to U.S. provisional application entitled, "Methods of Making Compounds," having Ser. No. 61/239,536, filed on Sep. 3, 2009, which is entirely incorporated herein by reference.

FEDERALLY-SPONSORED RESEARCH OR DEVELOPMENT

This invention was made with Government support under contract CA114747 awarded by the National Institutes of Health. The US Government has certain rights in this invention.

BACKGROUND

Some twenty years ago, the selective in vitro toxicity of the 2-deoxyguanosine analog, 9-β-D-arabinofuranosylguanine or AraG for T lymphoblasts was noted by several investigators. AraG is metabolized in a unique fashion by deoxyguanosine kinase and incorporated into mitochondrial DNA (FIG. 2.4). These observations led to the synthesis of a more water-soluble AraG prodrug, 2-amino-6-methoxypurine arabinoside (506U, Nelarabine), for potential clinical application in the treatment of T lymphoblastic diseases. This compound, developed over a number of years by Glaxo, is now FDA-approved for the treatment of relapsed T cell ALL and T cell lymphoblastic lymphomas.

SUMMARY

Embodiments of the present disclosure provide for compounds and methods of making compounds such as those shown in FIGS. 1.1A and 1.1B having formula 2, 3, 4, 5, 11, and 12 and formula 2', 3', 4', 5', and 11', as well as uses for the compounds for imaging, and the like.

An illustrative embodiment of making a labeled compound, among others, includes: reacting a compound including an isotope (Ist) with a compound having formula 1',

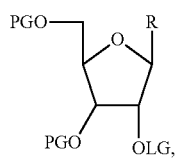

Formula 1' to form a compound having formula 2',

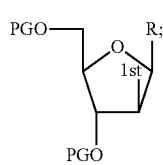

Formula 2' and conducting deprotection on the compound having formula 2' to form a compound having formula 3,

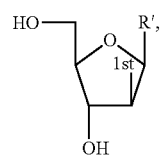

Formula 3 wherein PG is a protecting group and LG is a leaving group, and wherein R is a compound having a formula selected from the group consisting of R1, R2, R3, R4, R5, and R6:

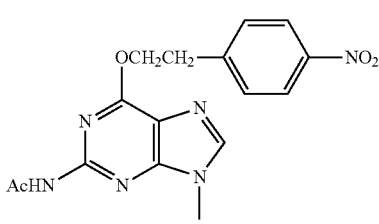

R1

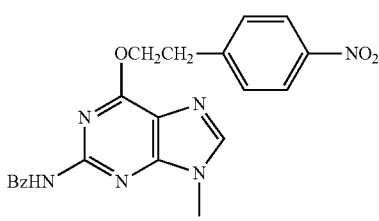

R2

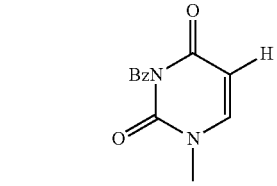

R3

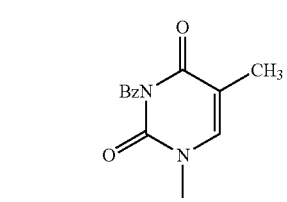

R4

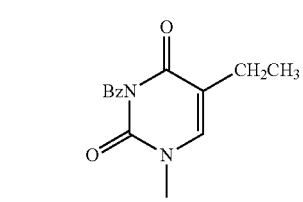

R5

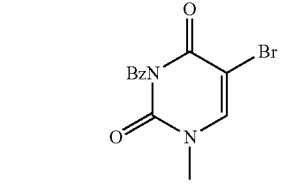

R6 and wherein R' is a compound having a formula selected from the group consisting of R'1, R'2, R'3, R'4, and R'5, wherein Ac is an acetyl group, and Bz is a benzoyl group, where each of Ac and Bz can be replaced as described herein:

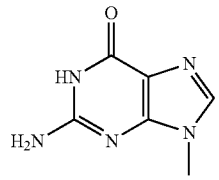
R'1

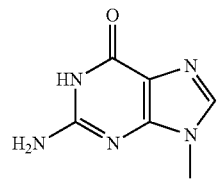
R'1

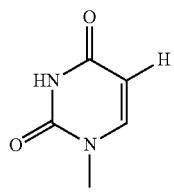
R'2

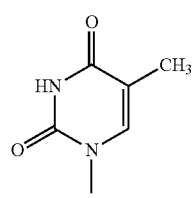
R'3

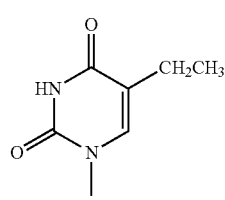
R'4

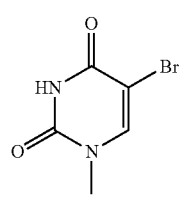
R'5

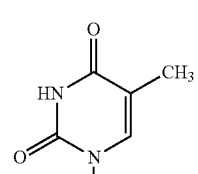
R'2

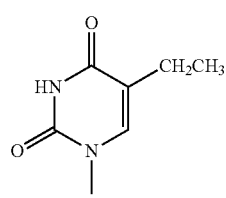
R'3

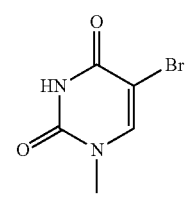
R'4

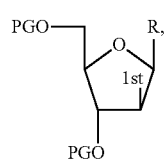
R'5

An illustrative embodiment of a labeled compound, among others, includes: a labeled compound, comprising: a compound having formula 3,

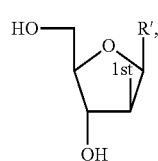

Formula 3 wherein Ist is an isotope, wherein R' is a compound having a formula selected from the group consisting of R'1, R'2, R'3, R'4, and R'5:

An illustrative embodiment of a labeled compound, among others, includes:

a compound having formula 2',

Formula 2' wherein PG is a protecting group, and wherein R is a group having a formula selected from the group consisting of R1, R2, R3, R4, R5, and R6:

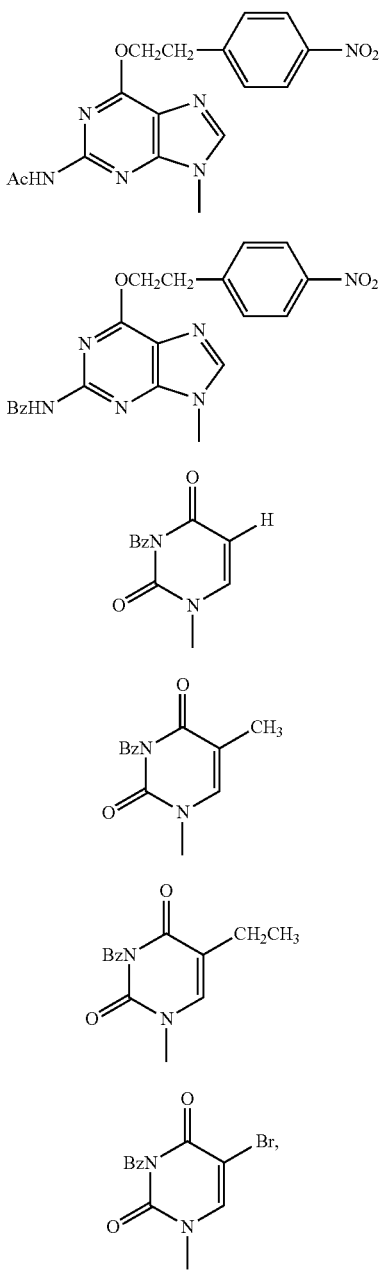

and wherein Ac is an acetyl group, and Bz is a benzoyl group, where each of Ac and Bz can be replaced as described herein.

An illustrative embodiment of the method of imaging a T Cell, among others, includes: administering to the subject a compound of the present disclosure; and imaging the subject, wherein detecting the presence of the compound corresponds to the presence of the T cell.

An illustrative embodiment of the imaging T lymphoblasts, among others, includes: administering to the subject a compound of the present disclosure; and imaging the subject, wherein detecting the presence of the compound corresponds to the presence of T lymphoblasts.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1.1A illustrates a number of synthesis schemes for making compounds of the present disclosure.

FIG. 1.1B illustrates a number of synthesis schemes for making compounds of the present disclosure.

FIG. 1.2 illustrates embodiments of R and R'.

FIG. 2.1 illustrates schematics of a synthesis of a [$^{18}$F]F-AraG precursor and [$^{18}$F]F-AraG.

FIG. 2.2 illustrates a graph of 5×10$^5$ CCRF-CEM cells were labeled with $^{18}$F-AraG (0.6 mCi/ml) for indicated times and doses. Uptake was measured on gamma counter. Bars represent mean of triplicate determinations+/−SEM.

FIG. 2.3a illustrates a graph of 5×10$^5$ CCRF-CEM cells were incubated, in triplicate, with 1 uCi 8H$^3$-AraG (1 mCi/ml) and increasing amounts of cold 2F-AraG or DMSO for either 60 or 120 minutes. Percent of control uptake was calculated as: measured cpm of sample/cpm accumulated 1 uCi 8[H$^3$]-AraG control×100.

FIG. 2.3b illustrates a graph of 5×10$^5$ CCRF-CEM, MOLT-4 or RAJI cells, in triplicate, were labeled with 1 uCi 8-$^3$H-AraG (1 mCi/ml) in the presence of 1 uM cold 2F-AraG, DMSO or media for 120 minutes. Percent of control uptake was calculated as in FIG. 2.3a.

FIG. 2.4 illustrates a schematic of the metabolism of 2'-deoxyguanosine (dGuo) by T lymphoblasts. In contrast to 2'-dGuo, AraG does not require ribonucleotide reductase activity for incorporation into DNA and is directly phosphorylated by mitochondrial dGK at low intracellular concentrations. At higher concentrations, it may also be phosphorylated by deoxycytidine kinase and incorporated into nuclear DNA. (Figure is from J Biol. Chem. 2008; 283:16437-16445).

FIG. 3.1 illustrates the analytical HPLC profile of co-injection of [$^{18}$F]F-AraG with cold F-AraG standard (5% acetonitrile: 95% water; 1 mL/min, 254 nm, Phenomenex Gemini C18, 5μ, 4.6×250 mm).

FIG. 3.2 illustrate a graph that shows 5×10$^5$ CCRF-CEM cells, in triplicate, that were exposed to either 3 μCi or 10 μCi of [$^{18}$F]F-AraG for 60 or 120 minutes. Cells took up ~2-fold more [$^{18}$F]F-AraG when exposed to 10 μCi, at 60 minutes (p=0.008) and at 120 minutes (p=0.001) as compared to 3 μCi. Error bars represent S.E.M.

FIG. 3.3 illustrates a graph that shows 1×10$^6$ purified primary T cells, stimulated with 100U/mL IL2, 50 nM PMA and 1 μg/mL ionomycin, or un-stimulated, were incubated for 60 minutes with 1 μCi of [$^{18}$F]F-AraG. Error bars represent mean of triplicate determinations+/−SEM., n=4 p=0.14 and 0.003 by two tailed, paired Student T test respectively.

FIG. 3.4 is a schematic diagram of scheme 1 that describes the synthesis of 2-N-Acetyl-6-O-((4-nitrophenyl)ethyl)-9-(3,5-di-O-trityl-2-trifyl-β-D-ribofuranosyl)guanine (2), the [$^{18}$F]F-AraG precursor.

FIG. 3.5 is a schematic diagram of scheme 2 that describes the synthesis of 2'-Deoxy-2'-fluoro-9-β-D-arabinofuranosylguanine 5 (F-AraG).

FIG. 3.6 is a schematic diagram of scheme 3 that describes the synthesis of 2'-deoxy-2'-[$^{18}$F]-fluoro-9-β-D-arabinofuranosylguanine 7 ([$^{18}$F]F-AraG).

DETAILED DESCRIPTION

Before the present disclosure is described in greater detail, it is to be understood that this disclosure is not limited to particular embodiments described, and the embodiment of the invention as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, chemistry, and the like, which are within the skill of the art. Such techniques are explained fully in the literature.

The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. Further, documents or references cited in this text, in a Reference List before the claims, or in the text itself; and each of these documents or references ("herein cited references"), as well as each document or reference cited in each of the herein-cited references (including any manufacturer's specifications, instructions, etc.) are hereby expressly incorporated herein by reference.

DEFINITIONS

As used herein, "alkyl" or "alkyl group" refers to a saturated aliphatic hydrocarbon radical which can be straight or branched, having 1 to 20 carbon atoms, wherein the stated range of carbon atoms includes each intervening integer individually, as well as sub-ranges. Examples of alkyl include, but are not limited to methyl, ethyl, n-propyl, i-propyl, n-butyl, s-butyl, t-butyl, n-pentyl, and s-pentyl. The term "lower alkyl" means an alkyl group having less than 10 carbon atoms.

The term "substituted," as in "substituted alkyl", "substituted phenyl," and the like means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. The term "lower alkoxy" means an alkoxy group having less than 10 carbon atoms.

In accordance with the present disclosure, "a detectably effective amount" of embodiments of the present disclosure is defined as an amount sufficient to yield an acceptable image using equipment that is available for clinical use. A detectably effective amount of the embodiments of the present disclosure may be given in one or more administrations. The detectably effective amount of embodiments of the present disclosure can vary according to factors such as the degree of susceptibility of the individual, the age, sex, and weight of the individual, idiosyncratic responses of the individual, the dosimetry, and the like. Detectably effective amounts of embodiments of the present disclosure can also vary according to instrument and film-related factors. Optimization of such factors may be within the level of skill in the art.

The term "detectable" refers to the ability to detect a signal or presence of an embodiment of the present disclosure over a background signal.

The term "detectable signal" or the phrases "detection of a labeled compound" or "detectable labeled compound" refers to the detection (directly or indirectly) of a labeled compound in a host or sample. The detection of a labeled compound refers to the ability to detect and distinguish the presence of a labeled compound in a host or sample from other background signals derived from the host or sample. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between detectable signal and the background. Standards and/or calibration curves can be used to determine the relative intensity of the detectable signal and/or the background. The detectable signal can be generated from a small to large concentration of a labeled compound. In an embodiment, the detectable signal may need to be the sum of each of the individual labeled compound signals. In an embodiment, the detectable signal can be generated from a summation, an integration, or other mathematical process, formula, or algorithm. In an embodiment, the summation, the integration, or other mathematical process, formula, or algorithm can be used to process the detectable signal so that the detectable signal can be distinguished from background noise and the like.

As used herein, "agent", "active agent", or the like, can include a compound (e.g., labeled compound) of the present disclosure. The agent can be disposed in a composition or a pharmaceutical composition.

As used herein, "pharmaceutical composition" refers to the combination of an active agent with a pharmaceutically acceptable carrier. As used herein, a "pharmaceutical composition" refers to a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use.

The term "unit dosage form," as used herein, refers to physically discrete units suitable as unitary dosages for human and/or animal subjects, each unit containing a predetermined quantity of a compound calculated in an amount sufficient (e.g., weight of host, disease, severity of the disease, etc) to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

The term "effective amount" as used herein refers to that amount of an embodiment of the present disclosure (which may be referred to as a labeled compound) being administered that can be used to image a cell such as a T Cell.

By "administration" is meant introducing an embodiment of the present disclosure into a subject. Administration can include routes, such as, but not limited to, intravenous, oral, topical, subcutaneous, intraperitoneal, intraarterial, inhalation, vaginal, rectal, nasal, introduction into the cerebrospinal fluid, or instillation into body compartments can be used.

As used herein, the term "host" or "subject" includes humans, mammals (e.g., cats, dogs, horses, etc.), and other living animals. In particular, the host is a human subject. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use as a "sample", such as mammalian (particularly primate such as human) blood, urine, or tissue samples, or blood, urine, or tissue samples of the animals mentioned for veterinary applications.

Discussion

Embodiments of the present disclosure provide for methods of making compounds such as those shown in FIGS. 1.1A and 1.1B having formula 2, 3, 4, 5, 11, and 12 and formula 2', 4', and 11', as well as uses for the compounds for imaging, for example. Embodiments of the present disclosure are advantageous because the compounds can be made in a few simple steps, as described in detail below and in Examples 1 to 3. In particular, embodiments of the present disclosure provide for the direct fluorination of a precursor of a guanosine nucleoside followed by removal of a protecting group. Embodiments of the method include two steps and these two steps occur over a short period of time, both of which are advantageous relative to other possible alternative commercial production schemes.

Embodiments of the method are shown in FIGS. 1.1A and 1.1B in schemes A to D and schemes A' to D'. Scheme A is generic, but uses specific protecting group (PG) and leaving group (LG), and schemes B to D provide additional details. Scheme A' to D' are generic in that they do not use specific protecting groups and leaving groups. It should be noted that the reagents can be changed in a manner similar to that described below. A more detailed scheme for an embodiment of the present disclosure is described in schemes 1 and 2 in Example 1 and Example 2.

In general, embodiments of the method include making a labeled compound such as those embodied in formulae 3, 5, and 12. In an embodiment, the method can include reacting a compound including an isotope (Ist) with a compound having formula 1 in FIG. 1.1A to form a compound having formula 2 in FIG. 1.1A. The synthesis described in FIGS. 1.1A and 1.1B are very similar, with the primary difference being the use of specific PG and LG in FIG. 1.1A. So the following discussion about the synthesis in FIG. 1.1A can be applied to the synthesis in FIG. 1.1B. The various substitutions for protecting groups, leaving groups, reactants, and the like, described herein can be used in the synthesis described in FIG. 1.1B.

R can be a group having a formula such as: R1, R2, R3, R4, R5, and R6 in FIG. 1.2. R' can be a structure having a formula such as R'1, R'2, R'3, R'4, and R'5 in FIG. 1.2. The selection of the R group may determine the R' group in formulae 3, 5, and 12.

It should be noted that Tr is trityle protecting group (PG), Tf is triflate leaving group (LG), Ac is a acetyl group, and Bz is a benzoyl group. Alternative protecting groups (PG) that can be used include protecting groups such as benzyl (Bn, Bnl), 6-methoxyethoxymethyl ether (MEM), methoxymethyl ether(MOM), p-methoxybenzyl ether (PMB), methylthiomethyl ether, methoxytrityl (MMT), pivaloyl (piv), terahydropyranyl (THP), trimethylsilyl (TMS), acetyl, difluoroacetyl, trifluoroacetyl, isobutyryl, benzoyl, 9-fluorenylmethoxycarbonyl, phenoxyacetyl, dimethylformamidine, N,N-diphenyl carbamate, or the like. Alternative leaving groups (LG) that can be used include tosylate, mesylates, alkylmsesylates, phenylsulfonates, nosylate, brosylate, actatae, alkyl acetaes, phenylacetaes, iodide, bromide, chloride, or the like. Alternative groups that can be substituted for the acetyl group include, carbobenzyoxy (cbz), p-methoxybenzy carbonyl (Moz), tet-Butyloxycarbonyl (BOC), 9-fluorenyl-methoxycarbonyl, phenoxyacetyl, dimethylformamidine, N,N-diphenyl carbamate, or the like. Alternative groups that can be substituted for the benzoyl group include, acetyl, difluoroacetyl, trifluoroacetyl, isobutyryl, 9-fluorenylmethoxy-carbonyl, phenoxyacetyl, dimethylformamidine, N,N-diphenyl carbamate, or the like. Thus, for each of the synthesis described, each of the PG, LG, Ac, and/or Bz can be substituted as described above and herein.

The isotope can be an isotope such as $^{18}F$, $^{131}I$, $^{125}I$, $^{124}I$, $^{123}I$, $^{121}I$, $^{77}Br$, $^{77}Br$, $^{75}Br$, or $^{75}Br$. In particular, the isotope can be $^{18}F$ as shown in scheme B in FIG. 1.1A. The compound containing an isotope can include $[^{18}F]KF$, $[^{131}I]NaI$, $[^{125}I]NaI$, $[^{124}I]NaI$, $[^{123}I]NaI$, $[^{121}I]NaI$, $[^{77}Br]NaBr$, $[^{77}Br]Br_2$, $[^{75}Br]NaBr$, or $[^{75}Br]Br_2$. In particular, the compounds containing the isotope can include $[^{18}F]KF$, as shown in scheme C in FIG. 1.1A. The amount of the precursor or starting material (formula 1) can be about 2 to 15 mg, which can be adjusted, along with other similar variables, depending on the amount of end product desired and the desired scale up of the synthesis.

The reaction can include appropriate solvents, reactive compounds, buffers, and the like. The reaction of the compound having formula 1 to form the compound of formula 2 can be conducted at a temperature of about 70 to 120° C. In regard to the amounts of the compounds used, the amount used can be scaled up or scaled down depending on the amount of the chemical desired to be produced.

In scheme C $[^{18}F]KF$ and 4,7,13,16,21,24-Hexaoxa-1,10-diazabicyclo[8.8.8]hexacosane (K2.2.2) are reacted in a solvent, DMSO, at about 85° C. to produce the compound having formula 4. An alternative reactive compound to 1,7,13,16,21,24-Hexaoxa-1,10-diazabicyclo[8.8.8]hexacosane can be selected from: 1,4,10-Trioxa-7,13-diaza-cyclopentadecane (K2.1), 4,7,13,16,21-Pentaoxa-1,10-diazabicyclo[8.8.5]tricosane (K2.2.1), 4,7,13,18-Tetraoxa-1,10-diazabicyclo[8.5.5]eicosane (K2.1.1), and 5,6-Benzo-4,7,13,16,21,24-hexaoxa-1,10-diazabicyclo[8.8.8]hexacos-5-ene (k2.2.2B). The amount of the reactive compound(s) can be about 20-50 mM in a solution of water (e.g., about 0.9 mL) and acetonitrile (e.g., about 0.1 mL). As noted above, the amounts or concentrations can be varied depending on the end product to be produced and the desired synthesis scale up.

In addition to DMSO, solvents such as acetonitrile, dimethylformamide, and combinations thereof can be used. Also, solvents such as THF, dioxane, sulfone and combinations thereof can be used. In an embodiment, $K_2CO_3$ and the reactive compound are disposed in water (e.g., about 0.9 mL) and acetonitrile (e.g., about 0.1 mL): 15 mM-30 mM and 20-50 mM, respectively. Also, an alternative to $K_2CO_3$ can be selected from $Na_2CO_3$, $Cs_2CO_3$, $Li_2CO_3$, and $Rb_2CO_3$.

Scheme D is similar to scheme C, but the R group is R1 in FIG. 1.2. As noted above, the R group can be any of R1 to R6 in schemes A to C.

Subsequently, the compound having formula 2, 4, or 11 is subjected to deprotection first with 0.5 M NaOCH$_3$ and then by 1N HCl at 100° C., for example, to form a compound having formula 3, 5, or 12 in FIG. 1.1A, the R' group can be any of R'1 to R'5 in FIG. 1.2. Alternatives to NaOCH$_3$ and HCl can be selected from MOR" or HX, respectively, where R" can be an alkyl or substituted alkyl group, or a phenyl group or a substituted phenyl group, and M could be Li, Na, K, Rb, or Cs, while X can be selected from F, Cl, Br, or I.

Compounds 2, 4, or 11 are then reacted with about 0.5 N NaOCH$_3$ in methanol (0.5 mL) at about 100° C. for about 10 min. After cooling the reaction mixture at room temperature, it was subjected to further acid deprotection with about 1N HCl (0.7 mL) at about 100° C. for about 10 min. Finally, after cooling the resulting reaction mixture at room temperature, it was neutralized to s pH of about 6-7 and the resulting solution was injected into a C18 reveres phase HPLC column to separate out the final product 3, 5 or 12. Also, an alternative to C18 reveres phase HPLC column purification is the use of series of C18 cartridges.

FIGS. 2.1 describe schemes 1 and 2, which are for a specific embodiment of the present disclosure, and are described in detail in Example 1. In particular, the $^{18}F$(FAraG precursor (compound 8) is produced and then reacted to form $^{18}F$ (FAraG precursor (compound 12). The details regarding the reaction steps are shown in FIG. 2.1, which are similar to those described above for the general synthesis. FIGS. 3.4 to 3.6 also provide specific details regarding the synthesis of embodiments of the present disclosure, and are described in detail in Example 2.

Embodiments of this disclosure also include methods of imaging T Cells and T lymphoblasts. In general, embodiments of the labeled compounds can be used to image the localization and/or quantity of T Cells and/or T lymphoblasts in subjects (e.g., a living human). The labeled compounds can be administered to the subject and then the subject or a portion of the subject can be imaged using a device such as Positron Emission Tomography (PET) to detect the presence and location within the subject, and/or quantity of the labeled compounds present. The presence and/or quantity can be used to detect the presence, location, and/or number/size of T Cells and/or T lymphoblasts at one or more locations in the subject.

Administration of the compounds (e.g., compositions, pharmaceutical compositions, and the like) can be via any of the accepted modes of administration for therapeutic agents. These methods include oral, parenteral, rectal, vaginal, nasal, inhaled, topical (including transdermal), parenterally, subcutaneous and other systemic modes.

Depending on the intended mode, the compositions including the labeled compounds may be in the form of solid, semisolid or liquid dosage forms, such as, for example, tablets, suppositories, pills, capsules, powders, liquids, suspensions, skin patch, or the like, preferably in unit dosage forms suitable for single administration of precise dosages. The compositions can include a conventional pharmaceutical excipient and a compound of the present disclosure.

Accordingly, an embodiment of the present disclosure is directed to a pharmaceutical composition comprising a pharmaceutically-acceptable carrier or excipient and a therapeutically effective amount of a compound of the present disclosure. Optionally, such pharmaceutical compositions may contain other therapeutic and/or formulating agents if desired. When discussing compositions, the "compound of the present disclosure" may also be referred to herein as the "active agent" or "agent". As used herein, the term "compound of the present disclosure" is intended to include a novel compound described in formulae provided herein and in the claims.

The pharmaceutical compositions of the present disclosure typically contain a therapeutically effective amount of a compound of the present disclosure. Typically, such pharmaceutical compositions can contain about 0.1 to about 95% by weight of the active agent; preferably, about 5 to about 70% by weight; and more preferably about 10 to about 60% by weight of the active agent.

The amount of the agent contacted (e.g., administered) can vary according to factors such as the degree of susceptibility of the individual, the age, sex, and weight of the individual, idiosyncratic responses of the individual, and the like. Detectably effective amounts of the agent of the present disclosure can also vary according to instrument and film-related factors. Optimization of such factors is well within the level of skill in the art.

The present disclosure can also provides packaged compositions including the precursor compounds or intermediates to the labeled compounds (e.g., formulae 1, 1', 2, or 2') and instructions for making the labeled compounds and methods of use (e.g., written instructions for their use). The kit can further include appropriate buffers and reagents known in the art for administering embodiments of the present disclosure to a subject.

EXAMPLES

The following examples are put forth so as to provide those of ordinary skill in the art with a complete disclosure and description of how to make and use the present disclosure, and are not intended to limit the scope of what the inventors regard as their disclosure nor are they intended to represent that the experiments below are all or the only experiments performed.

Example 1

Introduction

AraG is a nucleoside analog that has proven efficacy in the treatment of T cell lymphoblastic diseases. It is metabolized in a unique fashion by deoxyguanosine kinase and incorporated into mitochondrial DNA. We have synthesized the $^{18}$F derivative to use as a molecular probe. We will further examine the uptake and metabolism in cell lines and determine the efficacy of this compound in imaging T lymphoblasts in a mouse model and activated T cells in a mouse model of acute graft versus host disease. These data may lay a foundation for the use of this compound as an imaging agent in human disease.

Discussion

We have successfully synthesized a novel $^{18}$F derivative of 2-deoxyguanosine analog, 9-β-D-arabinofuranosylguanine (18F-AraG), to use as a molecular probe (FIG. 2.1). [$^{18}$F] AraG cell uptake was evaluated in leukemia cell line, CCRF-CEM, and was compared with [$^{3}$H]Arag cell uptake. FIG. 2.2 shows uptake of [$^{18}$F]AraG by CCRF-CEM cell and indicates that the uptake is dose dependent. To determine whether cold derivative 2F-AraG competes with the uptake of 8-[$^{3}$H]-AraG, we studied the [$^{3}$H]-Arag uptakes by CCRF-CEM, MOLT-4 (Leukemia cell line) and Raji (human Burkitt's lymphoma cell line) and competition with cold 2F-AraG (FIGS. 2.3a and 2.3b). FIG. 2.3a shows that increasing the amount of 2F-AraG (1-100 μM) causes decrease of the [$^{3}$H]-AraG uptake. Similar results were observed for MOLT4 and Raji cell lines (FIG. 2.3b). Competition assays indicate that cold derivative 2F-Arag competes with the uptake of the 8-[$^{3}$H]-AraG, indicating similar uptake pathways.

Initial micro PET scans in normal nude mice indicate that $^{18}$F-AraG is taken up within the thymus and lymph nodes.

FIG. 2.1 describes an embodiment of a method of making compounds of the present disclosure. The 2'-deoxy-2'-fluoroarabino nucleosides have been reported as antiviral agents (Proc Natl Acad Sci USA, 1992; 89: 2970-2974; Pharmacol 1999; 43: 233-240; J Pharm Chem 1996; 85: 339-344, each of which is incorporated herein by reference). We have been exploring the radio-labeled 8-[$^{18}$F]fluoroguanine derivatives as potential in-vivo probes for imaging gene expression with Positron Emission Tomography (PET). We have developed a method for the preparation of 8-[$^{18}$F]fluoroguanine derivatives based on a direct radiofluorination reaction and were able to synthesize 8-[$^{18}$F]fluoroguanosine from guanosine (Nuclear Medicine and Biology. 2000; 27(2): 157-162, which is incorporated herein by reference). Recently, the synthesis of 2'-deoxy-2'-[$^{18}$F]fluoro-9-β-D-arabinofuranosyladenine ([$^{18}$F]FAA) has been reported (J Label Comp Radiopharm 2003; 46: 805-814, which is incorporated herein by reference).

In our continuing efforts to synthesize new imaging probes, we are interested in the synthesis of 2'-deoxy-2'-[$^{18}$F] fluor-9-β-D-arabinofuranosylguanine ([$^{18}$F]FAraG). We have synthesized compound 8 in scheme 1 as a precursor for synthesis of [$^{18}$F]AraG. [$^{18}$F]FAraG was prepared from precursor 8 in 7-10% radiochemical (decay corrected) as shown in scheme 2. The synthesis utilizes the reaction between the leaving group triflate in 8 and [$^{18}$F] fluoride ion to produce [$^{18}$F]-labeled guanosine derivative 11. Deprotection of 11 produces the final [$^{18}$F]FAraG 12. No carrier-added [$^{18}$F] fluoride was prepared by the $^{18}$O(p,n)$^{18}$F nuclear reaction on a GE PETtrace cyclotron. [$^{18}$F]Fluoride processing and synthesis of [$^{18}$F]-labeled guanosine derivative 11 were completed in the GE TRACERlab FX-FN synthesis module. No carrier-added [$^{18}$F] fluoride trapped on a QMA cartridge was washed with a solution of $K_2CO_3$ (3.5 mg) and kryptofix 2.2.2 (15 mg) in water (0.9 mL) and acetonitrile (0.1 mL) (concentrations of $K_2CO_3$ and Kryptofix were 25.3 mM and 39.8 mM respectively). The solvent was removed under vacuum and to the anhydrous residue was added a solution of triflate precursor (compound 8, 4-6 mg) in DMSO (0.5 mL). The mixture was heated for 50 min at 85° C. and after cooling to room temperature, the reaction mixture was diluted with 1 mL $CH_3CN$ and 0.4 mL of water. The 18F-labeled intermediate 11 was purified by semi-prep HPLC. Compound 11 was reacted with 0.5 N $NaOCH_3$ in methanol (0.5 mL) at 100° C. for 10 min. After cooling the reaction mixture at room temperature, it was subjected to further acid deprotection with 1N HCl (0.7 mL) at 100° C. for 10 min. Finally, after cooling the resulting reaction mixture at room temperature, it was neutralized to pH 6-7 and the resulting solution was injected to a C18 reveres phase HPLC column to afford the final [$^{18}$] FAraG 12 in 7-10% radiochemical (decay corrected).

Example 2

Brief Introduction to Example 2

9-(β-D-Arabinofuranosyl)guanine (AraG) is a guanosine analog that has a proven efficacy in the treatment of T cell lymphoblastic disease. To test the possibility of using a radiofluorinated AraG as an imaging agent we have synthesized 2'-deoxy-2'-[$^{18}$F]fluoro-9-β-D-arabinofuranosylguanine ([$^{18}$F]F-AraG) and investigated its uptake in T-Cells.

To this end, we have synthesized [$^{18}$F]F-AraG via a direct fluorination of 2-N-acetyl-6-O-((4-nitrophenyl)ethyl)-9-(3', 5'-di-O-trityl-2'-O-trifyl-β-D-ribofuranosyl)guanine with [$^{18}$F]KF/K.2.2.2 in DMSO at 85° C. for 45 minutes. [$^{18}$F]F-AraG uptake in both a CCRF-CEM leukemia cell line (unactivated) and activated primary thymocytes was evaluated.

We have successfully prepared [$^{18}$F]F-AraG in 7-10% radiochemical yield (decay corrected) with a specific activity of 0.8-1.3 Ci/μmol. Preliminary cell uptake experiments showed that both a CCRF-CEM leukemia cell line and activated primary thymocytes take up the [$^{18}$F]F-AraG.

[$^{18}$F]F-AraG has been successfully synthesized by direct fluorination of an appropriate precursor of a guanosine nucleoside. This approach could be used for the synthesis of other important PET probes such as [$^{18}$F]FEAU, [$^{18}$F]FMAU and [$^{18}$F]FBAU which are currently synthesized by multiple steps and involve lengthy purification. The cell uptake studies support future studies to investigate the use of [$^{18}$F]F-AraG as a PET imaging agent of T-cells.

Materials and Methods

General:

Chemicals were purchased from Aldrich chemical company (Milwaukee, Wis.). 2',5'-Di-O-trityl guanosine derivative 1 (scheme 1 as shown in FIG. 3.4) was prepared from a partially protected 2-N-acetyl-6-O-((4-nitrophenyl)ethyl) guanosine derivative following a reported literature procedure (J. Org. Chem. 1992, 57, 7315-7321, which is incorporated herein by reference). Cold F-AraG standard (scheme 2 as shown in FIG. 3.5) was prepared according to the literature procedure (J. Org. Chem. 1992, 57, 7315-7321, which is incorporated herein by reference). HPLC grade acetonitrile ($CH_3CN$) and Millipore 18 m$\Omega$ water were used for [$^{18}$F]-AraG purifications which was performed on a Dionex Summit HPLC system (Dionex Corporation, Sunnyvale, Calif.) equipped with a 340 U 4-Channel UV-Vis absorbance detector and radioactivity detector (Carroll & Ramsey Associates, model 105S, Berkeley, Calif.). UV detection wavelengths were 218 nm, 254 nm and 280 nm for all the experiments. Semi preparative HPLC reverse phase column (Phenomenex, Hesperia, Calif., C18, 5μ, 10 mm×250 mm) was used for purification of [$^{18}$F]F-AraG. The mobile phase for the purification of [$^{18}$F]labeled 6 (scheme 3 as shown in FIG. 3.6) intermediate was water and acetonitrile. The eluent changed from 95% solvent A ($H_2O$) and 5% solvent B (acetonitrile) (0-2 min) to 35% solvent A and 65% solvent B at 10 min and to 5% solvent A and 95% solvent B at 36 min. The final [$^{18}$F]AraG was purified by semi preparative HPLC column with 5% acetonitrile in water as an eluent (isocratic). Radioactivity measurements were performed by A CRC-15R PET dose calibrator (Capintec Inc., Ramsey, N.J.). Electron spray ionization (ESI) mass spectrometry was done by Vincent Coates Foundation Mass Spectrometry Laboratory, Stanford University. $^1$H and $^{19}$F NMR spectra were taken on Mercury 400 MHz spectrometer.

Radiochemistry:

No carrier-added [$^{18}$F]fluoride was prepared by the $^{18}$O(p, n)$^{18}$F nuclear reaction on a GE PET tracer cyclotron. [$^{18}$F] Fluoride processing and synthesis of crude [$^{18}$F]labeled guanosine derivative 6 were completed in the GE TRACER lab FX-FN synthesis module.

Cell Uptake Studies:

CCRF-CEM (acute lymphoblastic T leukemia cell line procured form ATCC) cells were maintained in RPMI 1640 (Cellgro) supplemented with 100 U penicillin/100 ug streptomycin/ml (Cellgro) and 10% fetal bovine serum (Gibco). 5×10$^5$ CCRF-CEM cells were plated in 12 well dishes. Cells were allowed to settle for one hour then [$^{18}$F]F-AraG was added to each well and incubated at 37° C. for indicated times. Primary T cells were isolated from spleens and thymus of out-bred mice. Briefly, tissues were minced and single cell suspensions made in RPMI supplemented as above. Cells were centrifuged at 300×g for 8 minutes at 4° C. and cell pellets were resuspended in phosphate buffered saline (PBS) supplemented with 0.5% bovine serum albumin (BSA). T cells were purified from the suspensions using Miltenyi Pan T antibodies and columns (Miltenyi Biotec) per manufacturer's directions. Purified T cells were either stimulated with 100 U/ml IL-2 (eBiosciences) for 24 or 48 hours, or 50 nM phorbol myristate acetate (PMA) (Fluka) with 1 μg/mL ionomycin (Sigma) for 48 hours or left unstimulated then exposed to 1 μCi of [$^{18}$F]F-AraG/10$^6$ cells for 60 minutes. All cells were then washed in 1×PBS, lysed and radioactivity of each well was determined by gamma counter for [$^{18}$F] samples. All results were done in triplicate and are expressed in counts per minute (CPM), standard errors were determined and student T tests performed.

2-N-Acetyl-6-O-((4-nitrophenyl)ethyl)-9-(3,5-di-O-trityl-2-trifyl-β-D-ribofuranosyl)guanine (2)

Trifluoromethanesulfonyl chloride (44 μl, 0.42 mmol) in $CH_2Cl_2$ (1 mL) was added to a solution of 1 (0.20 g, 0.21 mmol) and DMAP (25 mg, 0.21 mmol) in $CH_2Cl_2$ (4.1 mL) containing triethylamine (58 μl, 0.21 mmol). The mixture was stirred for 1 h at room temperature and concentrated under vacuum. The crude triflate was purified by column chromatography (silica gel) using 1:1 chloroform and ethyl acetate as the eluent to afford 156 mg (68%) of 2 as a colorless viscous oil. $^1$H NMR (400 MHz, CDCl$_3$) δ ppm: 2.04 (3H, s, Ac), 2.64 (1H, d, H5', $J_{5'5''}$=11.2 Hz), 3.1 (1H, bs, H4'), 3.23 (1H, d, H5''), 3.34 (2H, t, (nitrophenyl)ethyl, J=6.9 Hz), 4.40 (1H, d, H3', $J_{2'3'}$=4.7 Hz), 4.81 (2H, t, (nitrophenyl)ethyl), 6.03 (1H, m, H2'), 6.64 (1H, d, H1', $J_{1'2'}$=7.8 Hz), 7.16-7.35 (30H, m, 2× trityl), 7.52 (2H, d, (nitrophenyl)ethyl, J=8.7 Hz), 7.68 (1H, s, NH), 8.09 (1H, s, H8), 8.18 (2H, d, (nitrophenyl)ethyl). $^{19}$F NMR (CDCl$_3$) δ ppm: −75.0 (s). High resolution MS: Calcd. MH$^+$ for $C_{59}H_{50}N_6O_{10}F_3S$: 1091.3261. Found 1091.3279.

6-O-((4-nitrophenyl)ethyl)-9-(3,5-di-O-trityl-2-fluoro-β-D-arabino-furanosyl)guanine (3)

Compound 1 (277 mg, 0.289 mmol) in dry $CH_2Cl_2$ (3 mL) was added to a solution of diethylaminosulfur trifluoride (DAST) (231 μl, 6 equiv) in dry $CH_2Cl_2$ (4 mL) containing pyridine (231 μl, 0.21 mmol). The mixture was stirred at room temperature overnight and diluted with $CH_2Cl_2$ (30 mL). The solution was subsequently washed with 5% NaHCO$_3$ (6 mL) and $H_2O$ (6 mL). After drying the organic fraction over with MgSO$_4$, the solvent was evaporated under vacuum. Crude product was purified by column chromatography (silica gel) using 4:1 chloroform and ethyl acetate as the eluent to afford 79 mg (30%) of 3 as a foam.
$^1$H NMR (400 MHz, CDCl$_3$) δ ppm: 3.16 (1H, dd, H5', $J_{5'4''}$=2.6 Hz, $J_{5'5''}$=10.0 Hz), 3.25-3.30 (3H, m, H5'', (nitrophenyl)ethyl), 3.72 (1H, dd, H2', $J_{1',2'}$=2.3 Hz, $J_{2',F}$=50.1 Hz), 4.24 (1H, dd, H3', $J_{3',4'}$=2.3 Hz, $J_{3',F}$=15.4 Hz), 4.49 (1H, m, H4'), 4.67-4.77 (2H, m, (nitrophenyl)ethyl), 4.88 (2H, bs, NH$_2$), 6.28 (1H, dd, H1', $J_{1',2'}$=2.3 Hz $J_{1',F}$=25 Hz), 7.20-7.41 (30H, m, 2×Tr), 7.46 (2H, d, (nitrophenyl)ethyl, J=8.7 Hz), 7.71 (1H, d, H8, $J_{8,F}$=3.7 Hz), 8.15 (2H, d, (nitrophenyl) ethyl). $^{19}$F NMR (CDCl$_3$) δ ppm: −196.11 (m).

9-(3,5-di-O-trityl-2-fluoro-β-D-arabinofuranosyl) guanine (4)

A solution of compound 3 (55 mg, 0.06 mmol) in dry pyridine (1.2 mL) containing DBU (91 mg, 0.6 mmol) was kept at room temperature for 15 h. The reaction mixture was neutralized to pH 6 with acetic acid and evaporated under vacuum. The residue was co-evaporated with toluene, dissolved in $CH_2Cl_2$ (4 mL) and the solution was washed with $H_2O$ (2×1 mL). After drying the organic fraction over with MgSO$_4$, the solvent was evaporated under vacuum and the crude product was purified by column chromatography (silica gel) using 95/5 CHCl$_3$ and $C_2H_5$OH as the eluent to afford 39 mg (85%) of 4 as a foam. $^1$H NMR (400 MHz, CD$_3$OD/CDCl$_3$) δ ppm: 3.09 (1H, dd, H5', J$_{5',4'}$=2.6 Hz, J$_{5',5''}$=10.1 Hz), 3.19 (1H, broad t, H5''), 3.65 (1H, d, H2' J$_{2',F}$=52.5 Hz), 4.15 (1H, d, H3', J$_{3',F}$=15.3 Hz), 4.39-4.41 (1H, m, H4'), 6.09 (1H, dd, H1', J$_{1',2'}$=1.7 Hz J$_{1',F}$=24.8 Hz), 7.15-7.33 (30H, m, 2×Tr), 7.51 (1H, d, H8, J$_{8,F}$=3.2 Hz). $^{19}$F NMR (CD$_3$OD/CDCl$_3$) δ ppm: −196.91.

2'-Deoxy-2'-fluoro-9-β-D-arabinofuranosylguanine (5, F-AraG)

A solution of compound 4 (35 mg, 0.046 mmol) in CF$_3$COOH—CHCl$_3$ (1:9, v/v, 0.45 mL) was kept at room temperature for 3 h. The residue was co-evaporated with toluene (350 μL), partitioned between CHCl$_3$ and water (2 mL: 2 mL). The aqueous layer was separated, neutralized with 5% NaHCO$_3$, and concentrated under vacuum. Product 5 (9.5 mg, 72%) was collected by filtration. $^1$H NMR (400 MHz, D$_2$O) δ ppm: 3.66 (1H, dd, H5', J$_{5',4'}$=5.7 Hz, J$_{5',5''}$=12.4 Hz), 3.73 (1H, dd, H5'', J$_{5'',4'}$=3.7 Hz), 3.91 (1H, approximately q, H4', J=5.0 Hz), 4.39 (1H, dm, H3', J$_{3',F}$=16.6 Hz), 5.07 (1H, dt, H2', J$_{1',2'}$=3.2 Hz, J$_{2',F}$=51.4 Hz), 6.13 (1H, dd, H1', J$_{1',2'}$=4.2 Hz J$_{1',F}$=17.5 Hz), 7.78 (1H, d, H8, J$_{8,F}$=2.6 Hz), $^{19}$F NMR (D$_2$O) δ ppm: −198.55 (1F, dt, F2', J$_{2',F}$=50.4 Hz, J$_{1',F}$=J$_{3',F}$=17.2 Hz). High resolution MS: Calcd. MNa$^+$ for C$_{10}$H$_{12}$N$_5$O$_4$FNa: 308.0771. Found 308.0783.

2'-Deoxy-2'-[$^{18}$F]fluoro-9-β-D-arabinofuranosylguanine (7, [$^{18}$F]-AraG)

No carrier-added [$^{18}$F]fluoride trapped on a QMA cartridge was eluted with a solution of K$_2$CO$_3$ (3.5 mg) and kryptofix 2.2.2 (15 mg) in water (0.9 mL) and acetonitrile (0.1 mL). The solvent was removed under vacuum at 65° C. and to the anhydrous residue was added a solution of triflate precursor (compound 2, 4-6 mg, scheme 3 as shown in FIG. 3.6) in DMSO (0.5 mL). The mixture was heated for 45 minutes at 85° C. After cooling to room temperature, the reaction mixture was passed through a silica gel cartridge and eluted with 3 mL of ethyl acetate. After ethyl acetate was removed under vacuum at 35° C., the residue was diluted to 1.5 mL with acetonitrile/water (80/20, v/v) and the resulting solution injected into a semipreparative HPLC column (Phenomenex Gemini, C18, 5μ, 10 mm×250 mm, 4 mL/min flow rate). The [$^{18}$F]6 was collected at 32 min and it was de-protected first by base (0.5 mL of 0.5M NaOCH$_3$) at 100° C. for 10 min and then by acid (0.5 mL of 1N HCl) at 100° C. for 10 min. After cooling to room temperature, the resulting solution was neutralized and injected into a C18 reverse phase semi preparative HPLC column. The product [$^{18}$F]F-AraG 7 was collected at 11.5 minutes and concentrated to dryness under vacuum at 45° C. Finally, [$^{18}$F]F-AraG 7 was reconstituted in saline and passed through a 0.22 μm Millipore filter into a sterile multidose vial for biological experiments. The radiochemical yield was 7-10% (decay corrected, n=10). The chemical and radiochemical purities of [$^{18}$F]F-AraG 7 was determined by reverse phase analytical HPLC method (Phenomenex Gemini C18, 5μ, 4.6×250 mm) and was more than 95% pure. The radio synthesis time was 140-160 min and the specific activity was 0.8-1.3 Ci/μmol.

Results
Chemistry:
Scheme 1, as shown in FIG. 3.4, shows the synthesis of 2-N-Acetyl-6-O-((4-nitrophenyl)ethyl)-9-(3,5-di-O-trityl-2-trifyl-β-D-ribiofuranosyl)guanine (2), the [$^{18}$F]F-AraG precursor. Treatment of 2',5'-di-O-trityl guanosine derivative 1 with CF$_3$SO$_2$Cl/DMAP afforded 2-N-acetyl-6-O-((4-nitrophenyl)ethyl)-9-(3',5'-di-O-trityl-2'-O-trifyl-β-D-ribofuranosyl)guanine (2) in 65% yield. Scheme 2, as shown in FIG. 3.5, shows the synthesis of cold F-AraG standard which was prepared according to the literature procedure (J. Org. Chem. 1992, 57, 7315-7321, which is incorporated herein by reference). 3',5'-Di-O-trityl guanosine derivative 1 was converted to 6-O-((4-nitrophenyl)ethyl)-9-(3',5'-di-O-trityl-2'-fluoro-β-D-arabinofuranosyl)guanine 3 with DAST reagent. De-protection of 3 with DBU afforded 9-(3',5'-di-O-trityl-2'-fluoro-β-D-arabinofuranosyl)guanine (4). Finally, de-protection of 4 by TFA afforded 2'-deoxy-2'-fluoro-9-β-D-arabinofuranosylguanine 5 (F-AraG).

Radiochemistry:
[$^{18}$F]-labeled guanosine derivative 6 (Scheme 3 as shown in FIG. 3.6) was prepared by nucleophilic displacement of triflate in 2 by [$^{18}$F]fluoride ion in DMSO at 85° C. for 45 min. Purification of [$^{18}$F]6 via HPLC was required to avoid contamination of the final product [$^{18}$F]F-AraG 7 with the de-protected starting material 2 (AraG). [$^{18}$F]6 was smoothly hydrolyzed first by base (0.5M NaOCH$_3$) and then by acid (1N HCl) to yield [$^{18}$F]F-AraG 7. The radiochemical yield was 7-10% (decay corrected, n=10) and the specific activity was 0.8-1.3 Ci/μmol. Analytical HPLC profile of co-injection of 7 with cold F-AraG standard is shown in FIG. 3.1.

Cell Uptake Assays
To evaluate the ability of cells to uptake [$^{18}$F]F-AraG, the CCRF-CEM cell line (acute lymphoblastic T leukemia cells, unactivated) and primary T-cells were exposed to [$^{18}$F]F-AraG. FIG. 3.2 shows the uptake of [$^{18}$F]F-AraG by unactivated CCRF-CEM cell and indicates that [$^{18}$F]F-AraG uptake is dose dependent with a 2-fold (P<XX) increase in [$^{18}$F]F-AraG uptake by cells exposed to 10 μCi compared to cells exposed to 3 μCi. We then looked to see if activated primary thymocytes derived from normal mouse tissue, would also accumulate [$^{18}$F]F-AraG. FIG. 3.3 represents the data that primary T cells stimulated with 100 U/mL of interleukin 2 take up 1.4-fold more (p=0.14) [$^{18}$F] F-AraG and primary T cells stimulate with 50 nM PMA and 1 μg/mL ionomycin take up 4.7 fold more (p=0.003) [$^{18}$F] F-AraG than un-stimulated primary T cells.

Discussion

There are many reports on the indirect synthesis of 2'-deoxy-2'-fluoro-9-β-D-arabinofuranosylguanine (F-AraG) in which fluorine is first introduced in the arabino position at C-2, and then fluorinated sugar reacted with the purine base (Carbohydr. Res. 1975, 42, 233-240, J. Org. Chem. 1985, 50, 3644-3647, and Chem. Pharm. Bull. 1989, 37, 336-339, each of which are incorporated herein by reference). However, there is only one report on the direct synthesis of cold F-AraG in which fluorine is incorporated into arabino position at C-2 of the sugar by direct fluorination of an appropriately protected guanosine derivative with DAST (J. Org. Chem. 1992, 57, 7315-7321, which is incorporated herein by reference). The synthesis of [$^{18}$F]labeled F-AraG has not been reported to date. Due to the difficult synthesis of [$^{18}$F]labeled DAST and long reaction times of DAST mediated fluorinations, it is not practical to synthesize [$^{18}$F]F-AraG via the [$^{18}$F]DAST method. Compound 2, the [$^{18}$F]F-AraG precursor was prepared (scheme 1 as shown in FIG. 3.4) and characterized by $^1$H and $^{19}$F NMR spectroscopy and high resolution mass spectrometry. Chemical shift of H2' changed from 4.73 ppm in 1 to 6.03 ppm in 2 due to the electronegativity of the trifyl group at C2' position. $^{19}$F NMR showed a singlet at −75.00 ppm which is consistent with the chemical shift of sugar triflates. Similar chemical shift trends were observed for the synthesis of adenosine triflate [19]. To the best of our knowledge precursor 2 is new and has been synthesized for the first time in our laboratory (provisional patent filed). Also, for the first time, we have synthesized [$^{18}$F]F-AraG (7, scheme 3 as shown in FIG. 3.6) via a direct fluorination of 2 with [$^{18}$F]KF/K.2.2.2 in DMSO in 7-10% radiochemical yield (decay corrected) with a specific activity of 0.8-1.3 Ci/μmol. The identity and purity of 7 was confirmed by co-injection with an authentic standard compound 5 on an analytical HPLC column (FIG. 3.1).

To evaluate the performance of [$^{18}$F]F-AraG 7 in cell culture, we performed several assays. To ascertain the ability of cells to uptake [$^{18}$F]F-AraG we exposed the CCRF-CEM cell line (acute lymphoblastic T leukemia cells, unactivated) and primary T-cells to [$^{18}$F]F-AraG. FIG. 3.2 shows the uptake of [$^{18}$F]F-AraG by CCRF-CEM cell and indicates that [$^{18}$F]F-AraG uptake is dose dependent. These data also support that a majority of the [$^{18}$F]F-AraG is taken up by cells within the first hour of exposure. The rapid uptake is necessary if [$^{18}$F] F-AraG, with an isotope half life of 110 minutes, is eventually going to prove efficacious as a PET tracer. Having ascertained that lymphoblastic T cell lines will take up [$^{18}$F]F-AraG, we then looked to see if primary T cells, non neoplastic T cells derived from normal mouse tissue, would also uptake [$^{18}$F] F-AraG. FIG. 3.3 represents the data of two independent experiments indicating that non neoplastic but activated primary T cells will take up [$^{18}$F]F-AraG to an appreciable level. The increased uptake of [$^{18}$F]F-AraG by activated T cells may enable one to utilize [$^{18}$F]F-AraG as a PET tracer in the detection of graft versus host disease (GVHD). GVHD is predominantly a T cell driven disease and the ability to detect aberrantly activated T cells by PET may facilitate an early diagnosis of GVHD in patients without invasive procedures. As AraG has been reported to induce neurotoxic side effects in some patients at therapeutic serum levels (~150 μM) [24], we chose to utilize doses lower (about 0.5 μM) than reported therapeutic levels of AraG in our assays to optimize [$^{18}$F]F-AraG as a tracer for PET while avoiding the potential neurotoxicity in PET patients.

CONCLUSION

For the first time to the best of our knowledge, [$^{18}$F]F-AraG has been successfully synthesized. This was accomplished by a direct fluorination method. This approach could be used for the synthesis of other important PET tracers such as [$^{18}$F] FEAU, [$^{18}$F]FMAU and [$^{18}$F]FBAU (J. Label. Radiopharm. 2003, 46, 285-289, which is incorporated herein by reference) which are currently synthesized by multiple steps and involve lengthy purification processes. Preliminary cell uptake experiments done in CCRF-CEM cells (unactivated) and activated primary T Cells suggest application of the [$^{18}$F]F-AraG as a new PET imaging agent for detection of disease of T cell origin.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A method of making a labeled compound, comprising:
reacting a compound including an isotope (Ist) with a compound having formula 1',

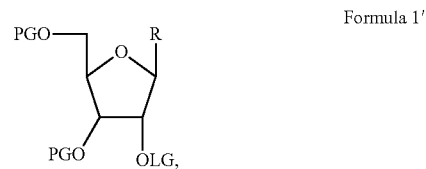

Formula 1' to form a compound having formula 2',

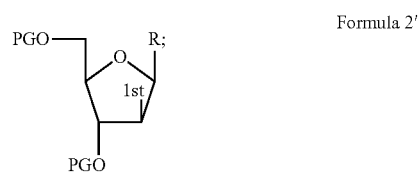

Formula 2' and
conducting deprotection on the compound having formula 2' to form a compound having formula 3,

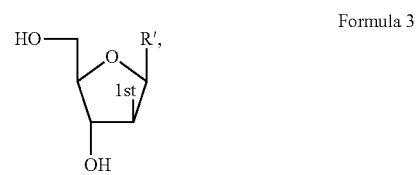

Formula 3 wherein PG is a protecting group and LG is a leaving group, and wherein R is a compound having a formula selected from the group consisting of R1, R2, R3, R4, R5, and R6:

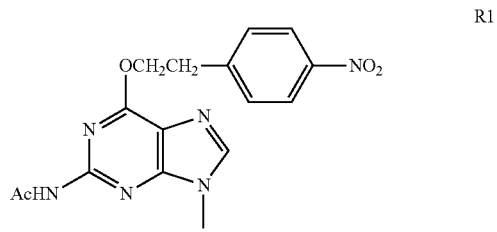

R1

-continued

R2
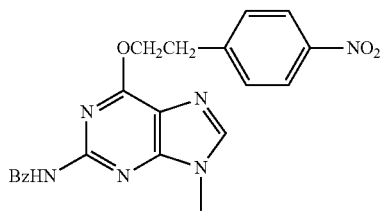

R3
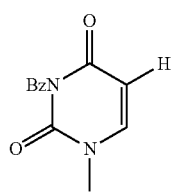

R4
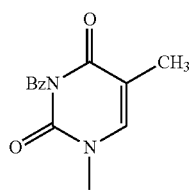

R5
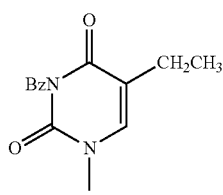

R6
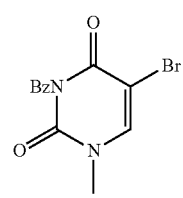

and wherein R' is
a compound having a formula selected from the group consisting of R'1, R'2, R'3, R'4, and R'5, wherein Ac is an acetyl group, and Bz is a benzoyl group:

R'1
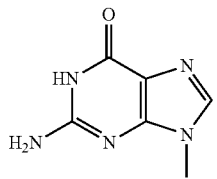

R'2
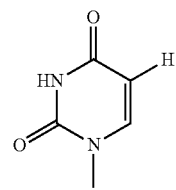

R'3
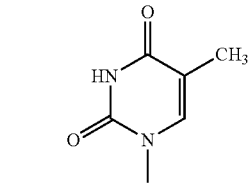

R'4
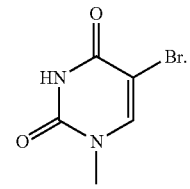

R'5
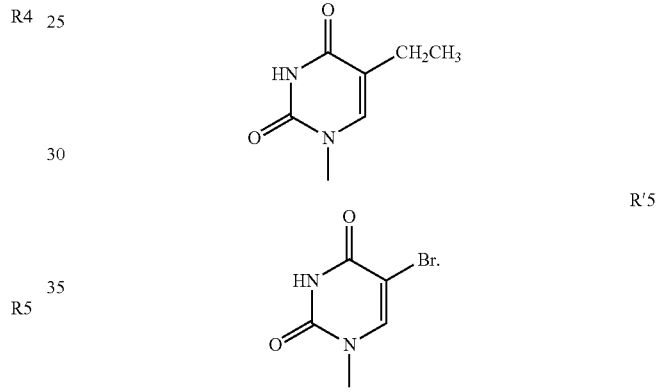

2. The method of claim 1, wherein the isotope is selected from the group consisting of: $^{18}F$, $^{131}I$, $^{125}I$, $^{124}I$, $^{123}I$, $^{121}I$, $^{77}Br$, and $^{75}Br$.

3. The method of claim 1, wherein the compound including the isotope is selected from the group consisting of: [$^{18}F$]KF, [$^{131}I$]NaI, [$^{125}I$]NaI, [$^{124}I$]NaI, [$^{123}I$]NaI, [$^{121}I$]NaI, [$^{77}Br$]NaBr, [$^{77}Br$]Br$_2$, [$^{75}Br$]NaBr, and [$^{75}Br$]Br$_2$.

4. The method of claim 1, wherein R is R1 or R2.

5. The method of claim 1, wherein reacting further includes a reactive compound selected from: 1,4,10-Trioxa-7,13-diaza-cyclopentadecane (K2.1), 4,7,13,16,21-Pentaoxa-1,10-diazabicyclo[8.8.5]tricosane (K2.2.1), 4,7,13,18-Tetraoxa-1,10-diazabicyclo[8.5.5]eicosane (K2.1.1), 5,6-Benzo-4,7,13,16,21,24-hexaoxa-1,10-diazabicyclo[8.8.8]hexacos-5-ene (k2.2.2B), 4,7,13,16,21,24-Hexaoxa-1,10-diazabicyclo[8.8.8]hexacosane (K2.2.2), and a combination thereof.

6. The method of claim 5, wherein the compound is 4,7,13,16,21,24-Hexaoxa-1,10-diazabicyclo[8.8.8]hexacosane (K2.2.2).

7. The method of claim 1, wherein reacting further includes a solvent selected from the group consisting of: dimethyl sulfoxide (DMSO), acetonitrile, dimethylformamide, and a combination thereof.

8. The method of claim 7, wherein the solvent is DMSO.
9. The method of claim 1, wherein the compound having formula 2' is a compound having formula 11',
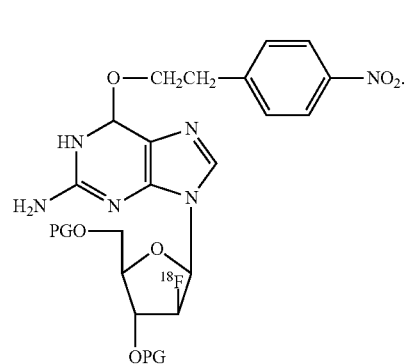
Formula 11'
10. The method of claim 9, wherein the compound having formula 3 is a compound having formula 12,
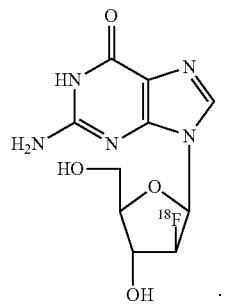
Formula 12
* * * * *